(12) United States Patent
Barrett et al.

(10) Patent No.: US 10,143,989 B2
(45) Date of Patent: Dec. 4, 2018

(54) STABILISATION FEATURES

(71) Applicant: GenCell Biosystems Ltd., Raheen, County Limerick (IE)

(72) Inventors: Brian Barrett, Cashel (IE); Patrick Tuohy, Roscrea (IE); Caitriona Ryan, Lahinch (IE); Mark McCabe, Dublin (IE)

(73) Assignee: GENCELL BIOSYSTEMS LTD., Raheen, County Limerick (IE)

( * ) Notice: Subject to any disclaimer, the term of this patent is extended or adjusted under 35 U.S.C. 154(b) by 390 days.

(21) Appl. No.: 14/761,470

(22) PCT Filed: May 7, 2014

(86) PCT No.: PCT/IB2014/001784
§ 371 (c)(1),
(2) Date: Jul. 16, 2015

(87) PCT Pub. No.: WO2014/188281
PCT Pub. Date: Nov. 27, 2014

(65) Prior Publication Data
US 2016/0045883 A1 Feb. 18, 2016

Related U.S. Application Data

(60) Provisional application No. 61/820,463, filed on May 7, 2013.

(51) Int. Cl.
| | | |
|---|---|---|
| B01L 7/00 | (2006.01) | |
| C12M 1/32 | (2006.01) | |
| B01L 3/00 | (2006.01) | |
| B01J 19/00 | (2006.01) | |
| G01N 33/48 | (2006.01) | |
| G01N 15/06 | (2006.01) | |

(52) U.S. Cl.
CPC ..... *B01J 19/0046* (2013.01); *B01L 3/502761* (2013.01); *B01J 2219/00306* (2013.01); *B01J 2219/00585* (2013.01); *B01J 2219/00596* (2013.01); *B01J 2219/00756* (2013.01); *B01L 7/52* (2013.01); *B01L 2200/0668* (2013.01); *B01L 2200/0673* (2013.01); *B01L 2200/0684* (2013.01); *B01L 2300/161* (2013.01); *C12M 23/12* (2013.01)

(58) Field of Classification Search
None
See application file for complete search history.

(56) References Cited

U.S. PATENT DOCUMENTS 5,065,768 A * 11/1991 Coleman ............. B01L 3/50825
422/916
6,184,029 B1 * 2/2001 Wilding ............. B01D 67/0062
204/193

(Continued)

FOREIGN PATENT DOCUMENTS

JP 2005169386 A 6/2005
WO WO 2007/024778 A2 3/2007
(Continued)

*Primary Examiner* — Jill A Warden
*Assistant Examiner* — Brittany I Fisher
(74) *Attorney, Agent, or Firm* — Kathleen Y. Rao; Bret E. Field; Bozicevic, Field & Francis LLP

(57) ABSTRACT

Devices, systems and methods for making and handling liquid samples are disclosed.

12 Claims, 7 Drawing Sheets

(56) References Cited

U.S. PATENT DOCUMENTS

| | | | |
|---|---|---|---|
| 8,092,432 B2 | 1/2012 | Nordgren | |
| 8,192,841 B2 * | 6/2012 | Amundson | A61K 8/0208 |
| | | | 428/402 |
| 9,194,772 B2 | 11/2015 | Lee et al. | |
| 2002/0050659 A1 * | 5/2002 | Toreki | A01N 25/006 |
| | | | 264/4.1 |
| 2005/0148066 A1 * | 7/2005 | O'Keefe | B01F 13/0071 |
| | | | 435/287.2 |
| 2005/0266582 A1 * | 12/2005 | Modlin | B01L 3/5027 |
| | | | 436/164 |
| 2007/0264705 A1 * | 11/2007 | Dodgson | A61B 17/435 |
| | | | 435/283.1 |
| 2010/0028207 A1 * | 2/2010 | Colella | B01L 3/502715 |
| | | | 422/73 |
| 2011/0003286 A1 * | 1/2011 | Hanafusa | B01L 3/5025 |
| | | | 435/6.12 |
| 2011/0226339 A1 | 9/2011 | Aoki et al. | |
| 2012/0045765 A1 * | 2/2012 | Curran | B01F 13/0071 |
| | | | 435/6.12 |
| 2013/0059322 A1 * | 3/2013 | Hung | C12M 23/12 |
| | | | 435/29 |

FOREIGN PATENT DOCUMENTS

| | | |
|---|---|---|
| WO | WO 2007/024798 A2 | 3/2007 |
| WO | WO 2007/024800 A2 | 3/2007 |
| WO | WO 2007/024914 A2 | 3/2007 |
| WO | 2012011091 A2 | 1/2012 |
| WO | 2013111016 A2 | 8/2013 |
| WO | 2014083435 A2 | 6/2014 |
| WO | 2014207577 A2 | 12/2014 |
| WO | 2015075560 A2 | 5/2015 |
| WO | 2015075563 A2 | 5/2015 |

\* cited by examiner

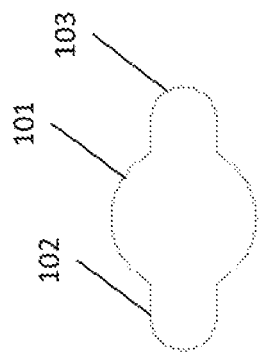
FIGURE 1
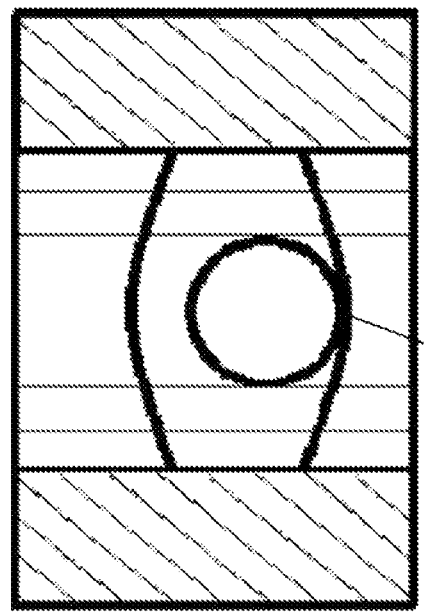
FIGURE 2
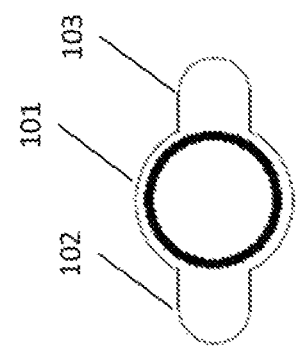

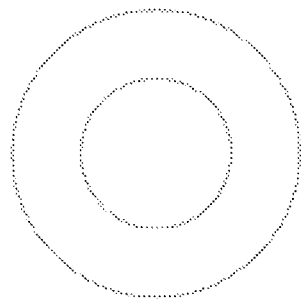
FIGURE 3
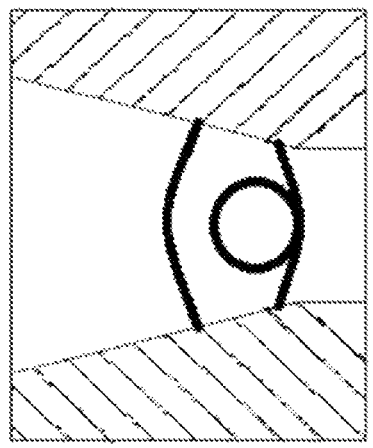
FIGURE 4
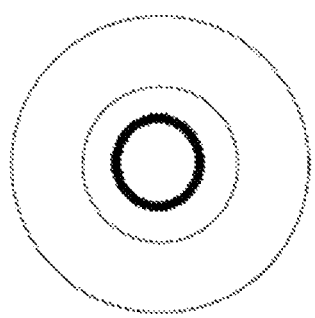

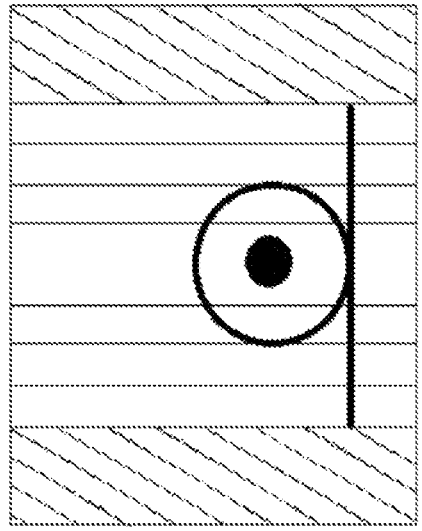
FIGURE 5
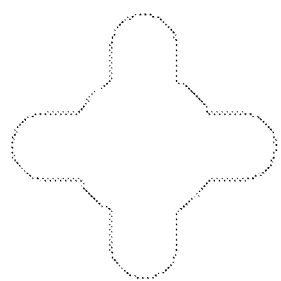
FIGURE 6
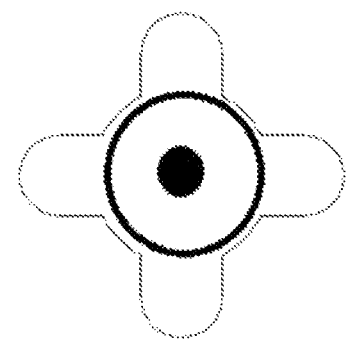

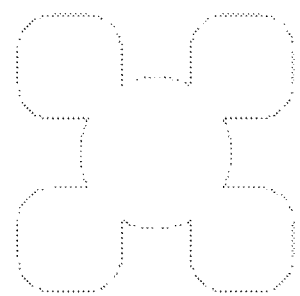
FIGURE 11
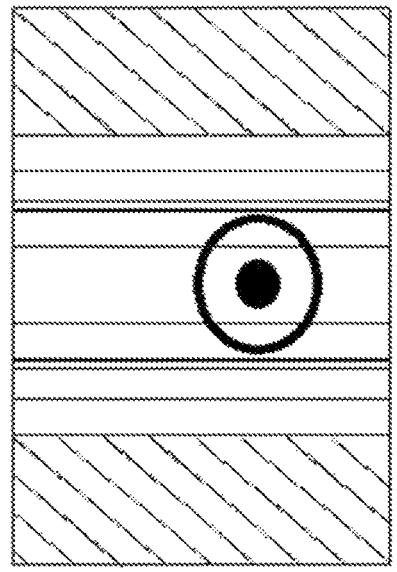
FIGURE 12
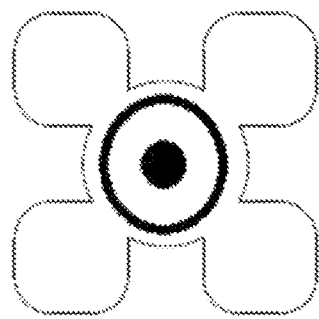

STABILISATION FEATURES

RELATED APPLICATIONS

This application claims the benefit of U.S. provisional application Ser. No. 61/820,463, filed May 7, 2013, which is hereby incorporated herein by reference in its entirety.

Also incorporated herein by reference in their entirety are U.S. provisional application Ser. Nos. 61/344,434, filed Jul. 22, 2010, 61/470,515, filed Apr. 1, 2011, 61/470,520, filed Apr. 1, 2011, and 61/590,499, filed Jan. 25, 2012, and U.S. utility application Ser. No. 13/147,679, filed Aug. 3, 2011.

BACKGROUND

Currently the processing of biological samples has a number of key drawbacks. These include the requirement for relatively large volume reaction volumes—resulting in high reagent costs; high consumable costs; and labour-intensive protocols and processes, which are highly susceptible to cross-contamination. For these reasons complete control and isolation of each individual sample within the biochemistry process cannot currently be ensured. Composite liquid cells (CLCs), as described in U.S. utility application Ser. No. 13/147,679, offer solutions to many such problems.

Some applications of CLCs involve heating reagents and biological samples contained in a CLC. Such applications can include cell screening, immunoassays, nucleic/ribonucleic acid sample extractions, nucleic acid isolation/purifications, various different methods of nucleic acid amplification (including PCR, dPCR, qPCR, TMA, bDNA, LCR, etc), and nucleic acid library preparation for sequencing. Occasionally a CLC may contain a gas, for example, ambient air that has been trapped in or absorbed by the CLC, or gaseous by-products of chemical reactions taking place inside the CLC. The presence of gas in a CLC, especially a CLC undergoing thermal changes, can create problems in handling, aligning, stabilizing and/or immobilizing the CLC, problems that might not exist in a larger reaction volume. Misalignment can be a particular problem for optical detection systems that rely on accurate placement of the CLC at a predetermined site.

SUMMARY

Devices, systems and methods for making and handling liquid sample's are disclosed.

BRIEF DESCRIPTION OF THE DRAWINGS

FIGS. 1-12 schematically show various liquid cell stabilisation features from above, and in side cross-section, in some cases including stabilized CLCs.

DETAILED DESCRIPTION

Figure 7:
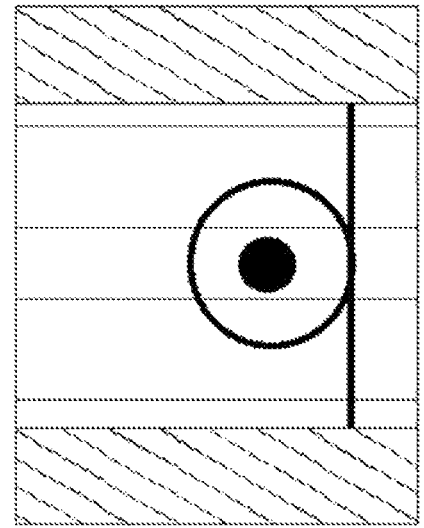
Figure 7:

To avoid the problems associated with gases retained in CLCs, one can, for example minimize the likelihood that CLCs will be formed containing gas in the first place, minimize the degree to which gas enters a previously formed CLC, or encourage gas present in a CLC to exit the CLC.

Degassing some or all of the reaction components prior to processing can result in CLCs that contain less gas than would otherwise be present. A typical method of degassing a fluid is to place it in negative pressure to remove any dissolved gases. Heating and/or agitating the fluid while under negative pressure can augment this process. This method can significantly reduce the presence of, if not 100% removing, dissolved gases. Following heating, agitation and/or the application of negative pressure, the degassed liquid can be stored in a vacuum-sealed vessel. Ideally, the degassed fluid is typically used immediately or shortly after processing to minimise the reabsorption of gases.

In static systems, optical detection can be employed to track any gas production and account for the resulting movement, reaction loss or reduction in data quality. Optical detection systems are typically expensive, complicated to integrate, and require extensive computational power to work effectively.

As explained in U.S. utility Pat. No. 8,465,707, stabilisation features can be used to immobilize or hinder CLCs, and may be part of the process of creating, moving, mixing, combining, splitting, processing and/or otherwise controlling CLCs on the free surface of a carrier fluid. The shape of the stabilisation feature can be designed to encourage the exit of gases from a CLC.

FIG. 1 schematically shows an overhead view of a stabilisation feature having a generally round central portion 101 and two channels 102, 103. FIG. 2 shows the same stabilisation feature with a droplet 104 of encapsulating fluid stabilized in the central portion. The stabilisation feature is shown from above and in cross-section from the side. The channels 102, 103 allow for and encourage the escape of gases from the encapsulating fluid. The escaped ins may either be trapped in the channels 102, 103 or may escape the stabilisation feature entirely. Exit of gases from the CLC or encapsulating fluid can prevent the CLC from floating off the stabilisation feature, and can improve the repeatability of locating the CLC on the stabilisation feature. Without the channels, gas might be retained within the CLC; because of the shape of the stabilisation feature, any gas released by the CLC can exit.

FIGS. 3 and 4 similarly show schematically a stabilisation feature that allows or encourages gas to escape from a CLC. In this case, the stabilisation feature defines a generally frustoconical void with the free surface of the carrier fluid at the bottom of the frustum. The CLC sits on the free surface of the carrier fluid, and the upwardly opening conical shape encourages gas to escape from the CLC.

FIGS. 5 and 6 are schematically show an embodiment similar to that shown in FIGS. 1 and 2 but with four symmetrically positioned channels rather than two.

Figure 8:
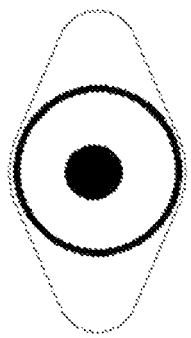

FIGS. 7 and 8 schematically show a generally diamond-shaped stabilisation feature, where the short axis of the diamond retains the CLC, and the long axis of the diamond defines channels through which gases may escape.

Figure 9:
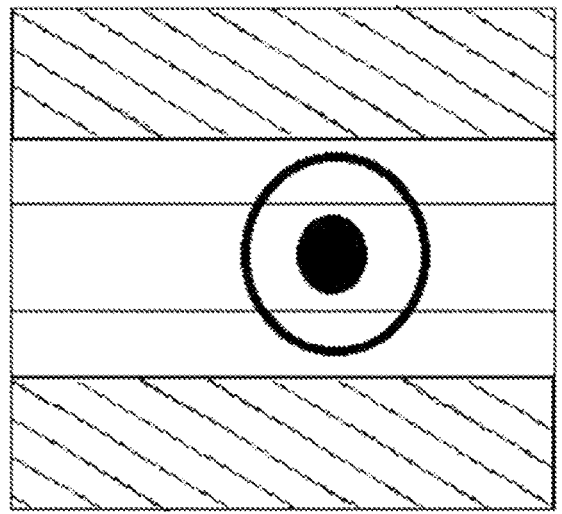
Figure 9:
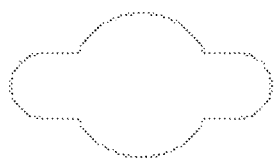
Figure 10:
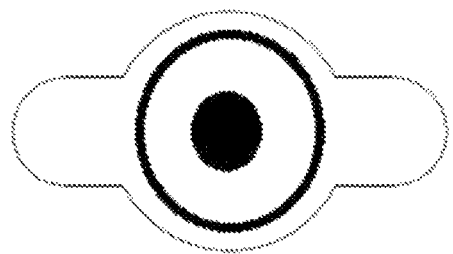

FIGS. 9 and 10 schematically show a stabilisation feature similar to that of FIGS. 1 and 2.

FIGS. 11 and 12 schematically show a generally cloverleaf-shaped stabilisation feature with four exterior channels for gas escape.

As used herein, control surface can mean any material that contacts any of the fluids. For example, stabilisation features can be part of the control surface, as can canals or other connections. Controllers, such as control rods, control tubes, capillary metering tubes, etc., designed to move, immobilize, create, combine or otherwise manipulate CLCs or their constituent fluids, can also be a control surface.

Figure 13:
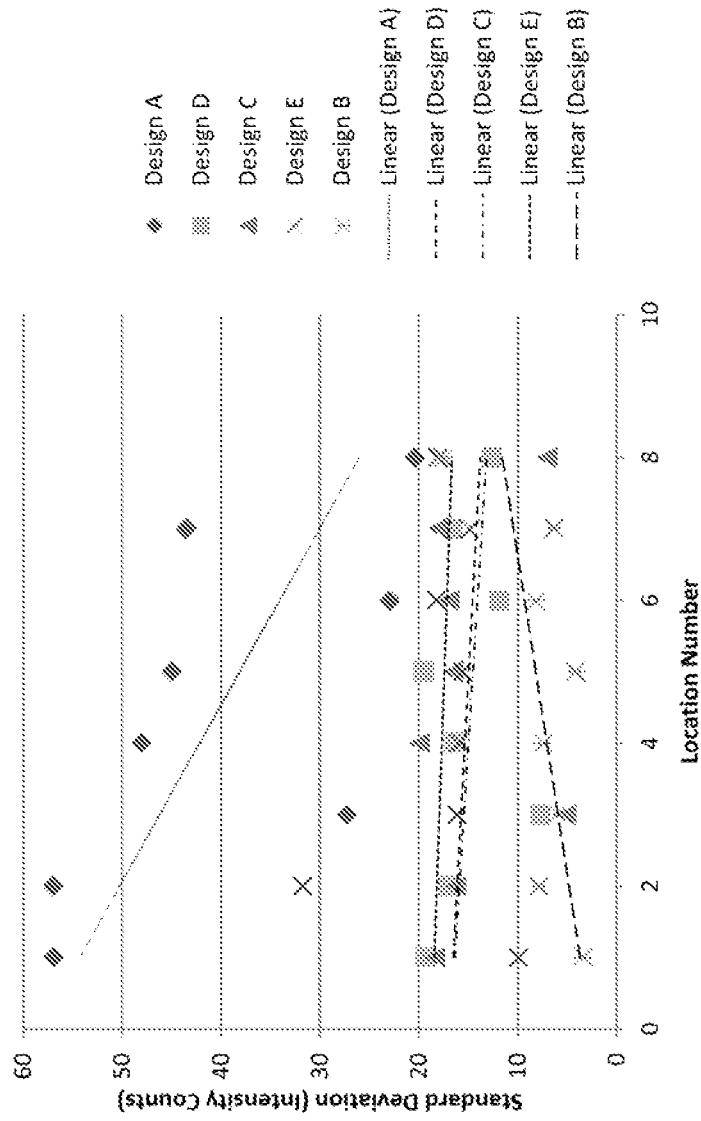
FIG. 13 is a plot of the standard deviation of intensity at each of eight nodes with various different geometric gas stabilisation features and with no geometric gas stabilisation features.

FIG. 13 is a graph showing improvement in location consistency due to the use of gas stabilisation features.

Design A included no features designed to encourage gas to exit the CLCs. Designs B, C, D and E included features such as those shown in FIGS. 1-12. CLCs were formed with artificially introduced gases, and then located at each of 8 stabilisation features in each of designs A-E. The CLCs were then optically interrogated. The experiment was repeated multiple times for each design. At each location the standard deviation of the detected optical counts was calculated and is shown in FIG. 13. Design A performs the worst, having the largest standard deviation of intensity counts. Designs B, C, D and E perform better, with the best design B, lowering the standard deviation six-fold or more in some cases.

In some embodiments the control surfaces have a circular shape.

In some embodiments the stabilisation feature consists of circular through-hole that is hydrophobic. The through-hole is generated in a hydrophobic material.

In another embodiment the control surface is formed in a material coated with a hydrophobic material.

As explained in U.S. utility Pat. No. 8,465,707, stabilisation features can have a variety of shapes and functions. Some are connected by "canals" in a network. In some cases, the canals in a network can serve the same function to encourage the exit of gases as the channels shown in FIGS. 1-12.

To eliminate the problem of movement of the composite liquid cells the control surfaces are shaped to allow gases to escape, while maintaining the composite liquid cell in the optimum position for processing, for example, in liquid handling, thermal processing, and/or during optical detection.

In one embodiment the control surface shape provides a preferential location for gases, to prevent interference with the composite liquid cell.

One embodiment of this invention uses the density differences of fluids to ensure gas free operation.

One embodiment the control surfaces allow fluid communication between composite liquid cell locations.

Example Node Shapes

In one embodiment the stabilisation feature has a tapered vertical profile, creating a funnel shape, a narrow base and wider top dimension as in FIG. 4. The shape can be frustoconical as shown, or any other sort of taper.

In one embodiment the taper is wider at the top than the bottom.

A preferred shape is that of a circular shape with one or more smaller geometrical shapes offset from a central location for the composite liquid cell as in FIGS. 1-12

In one embodiment the shape is that of a semi-circle, see FIG. 9

In one embodiment the shape is an elongated channel.

In one embodiment the control surfaces are stationary

In one embodiment the control surfaces move.

In one embodiment the control surfaces move and the shape features are parallel to the direction of motion.

In one embodiment the control surfaces move and the shape features are perpendicular to the direction of motion.

In one embodiment the control surfaces move and the shape features are diagonal to the direction of motion.

In one embodiment the control surfaces are heated.

Stabilisation Method

In one embodiment an encapsulating fluid is deposited on the free surface of a carrier fluid. The encapsulating fluid is then heated or cooled. A biological sample is then dispensed, generating a composite liquid cell.

In one embodiment an encapsulating fluid is deposited on the free surface of a carrier fluid. A biological sample is then dispensed, generating a composite liquid cell. The cell is then heated or cooled prior to biological processing.

In one embodiment the heating or cooling is rapidly performed.

In one embodiment the encapsulating fluid is returned to ambient temperature.

In one embodiment the encapsulating fluid is maintained at a thermal set point for biological processing.

In one embodiment an encapsulating fluid is deposited on the free surface of a carrier fluid. The encapsulating fluid is then agitated. A biological sample is then dispensed, generating a composite liquid cell.

In one embodiment an encapsulating fluid is deposited on the free surface of a carrier fluid. A biological sample is then dispensed, generating a composite liquid cell. The composite liquid cell is then agitated prior to biological processing.

In one embodiment the agitation is mechanical.

In one embodiment the agitation is fluidic.

In one embodiment the agitation is pressure induced.

Certain Specific Embodiments

A stabilization feature can be used to immobilize a composite liquid cell. The stabilization feature can include a hydrophobic wall defining a vessel. The vessel can define a central portion sized and shaped to snugly contain a composite liquid of a predetermined size, a vertical axis, and at least one channel portion adapted to flow gas away from the central portion. The vessel generally defines a cross-sectional shape in a plane perpendicular to the vertical axis. In some embodiments the cross-sectional shape is constant along the vertical axis. In some embodiments the cross-sectional shape is not constant along the vertical axis. For example, the vessel may be tapered so that the cross-sectional shape is larger at or near one end of the vessel than at or near the other end of the vessel.

In some embodiments the central portion can be substantially circular. In some embodiments the cross-sectional shape can be, for example, substantially rhomboid, or circular, or cloverleaf-shaped.

In some embodiments the at least one channel portion can be substantially circular, or substantially rectangular. In some embodiments the at least one channel portion can be offset horizontally from the central portion. In some embodiments the at least one channel portion is a plurality of channel portions, while in other embodiments the at least one channel portion is a single channel portion. A plurality of channel portions can be evenly or unevenly circumferentially spaced around the vertical axis. For example, two channel portions can be spaced 180 degrees apart from one another around the vertical axis, or four channel portions can be spaced 90 degrees apart from one another around the vertical axis.

In some embodiments a stabilization feature for immobilizing a composite liquid cell can include a hydrophobic wall defining a vessel. The vessel can define a central portion sized and shaped to snugly contain a composite liquid of a predetermined size, and a vertical axis. The vessel can have a cross-sectional shape in a plane perpendicular to the vertical axis, and the cross-sectional shape can be tapered along the vertical axis so that the area of the cross-sectional shape is larger at a top of the vertical axis than at a bottom of the vertical axis. In some embodiments the vessel can have a plurality of cross-sectional shapes each in a plane perpendicular to the vertical axis, and all of the plurality of cross-sectional shapes are congruent. In some embodiments, the plurality of cross-sectional shapes are not all congruent. For example, near the bottom the cross-sectional shape might be substantially circular, while near the top the cross-sectional shape could be substantially rectangular or substantially clover-leaf-shaped. In some such embodiments, the vessel might include one or more channel portions that extend downward from the top of the vessel, but do not reach the bottom of the vessel.

In some embodiments, a plurality of stabilization features can be part of a network. The stabilization features in the network can be connected by a plurality of canals. Each stabilization feature can be in fluid communication with one or more other stabilization features by way of one or more canals. In some embodiments, such a network can include a carrier liquid having a substantially horizontal free surface, and the central portion of each vessel can include a predetermined quantity of an encapsulating liquid. The carrier liquid can be immiscible with the encapsulating liquid and denser than the encapsulating liquid so that the encapsulating liquid floats on the free surface of the carrier liquid.

A method can include providing such a network that includes stabilization features connected by canals. The method can include charging the plurality of canals and the stabilization features with a sufficient quantity of a carrier liquid that the carrier liquid has a substantially horizontal free surface throughout all the canals and stabilization features, drawing a predetermined quantity of an encapsulating liquid from an encapsulating liquid input, discharging the drawn predetermined quantity of encapsulating liquid proximate to one of the plurality of stabilization features, wherein the carrier liquid is immiscible with the encapsulating liquid and denser than the encapsulating liquid so that the predetermined quantity of encapsulating liquid floats on the free surface of the carrier liquid, drawing a predetermined quantity of a sample liquid from a sample-liquid input, and discharging the drawn predetermined quantity of sample liquid proximate to the discharged predetermined quantity of encapsulating liquid to form a composite liquid cell on the free surface of the carrier liquid, the sample liquid being immiscible with the encapsulating liquid and with the carrier liquid, so that the sample liquid does not mix with either the encapsulating liquid or with the carrier liquid.

In some embodiments, such methods can include either heating or cooling the discharged predetermined quantity of encapsulating liquid. The heating or cooling can be carried out either prior to, during, or after discharging the predetermined quantity of sample liquid. In some such methods, the composite liquid cell can be maintained a predetermined thermal set point a predetermined amount of time as part of a biological processing protocol.

We claim:

1. A stabilization feature for immobilizing a composite liquid cell, the stabilization feature comprising:
   a hydrophobic wall defining a vessel;
   wherein:
      the vessel defines a central portion sized and shaped to snugly contain a composite liquid cell of a predetermined size;
      the vessel defines a vertical axis; and
      the vessel defines at least one channel portion adapted to flow gas away from the central portion and having walls continuous with the wall defining the vessel; and
      the vessel has a cross-sectional shape that comprises the cross-sectional shape of the at least one channel portion.

2. The stabilization feature of claim 1 wherein the vessel has a cross-sectional shape in a plane perpendicular to the vertical axis, and the cross-sectional shape is constant along the vertical axis.

3. The stabilization feature of claim 1 wherein the vessel has a cross-sectional shape in a plane perpendicular to the vertical axis, and the cross-sectional shape is not constant along the vertical axis.

4. The stabilization feature of claim 3 wherein the vessel is tapered so that the cross-sectional shape is larger higher along the vertical axis.

5. The stabilization feature of claim 1 wherein the central portion is substantially circular.

6. The stabilization feature of claim 1 wherein the at least one channel portion is offset horizontally from the central portion.

7. The stabilization feature of claim 1 wherein the at least one channel portion is a plurality of channel portions.

8. The stabilization feature of claim 7 wherein the plurality of channel portions is two channel portions spaced 180 degrees apart from one another around the vertical axis.

9. The stabilization feature of claim 7 wherein the plurality of channel portions is four channel portions spaced 90 degrees apart from one another around the vertical axis.

10. The stabilization feature of claim 1 wherein the at least one channel portion is substantially circular.

11. The stabilization feature of claim 1 wherein the at least one channel portion is substantially rectangular.

12. The stabilization feature of claim 1 wherein the cross-sectional shape is substantially rhomboid.

\* \* \* \* \*